US00PP34790P2

(12) United States Plant Patent
Zarnowski et al.

(10) Patent No.: US PP34,790 P2
(45) Date of Patent: Dec. 6, 2022

(54) HAZELNUT TREE NAMED 'PHOTON'

(50) Latin Name: ***Corylus americana* X *Corylus avellana***
Varietal Denomination: Photon

(71) Applicant: Z''s Nutty Ridge LLC, McGraw, NY (US)

(72) Inventors: Jeffrey J. Zarnowski, McGraw, NY (US); Dawn M. Zarnowski, McGraw, NY (US)

(73) Assignee: Z's Nutty Ridge, LLC, McGraw, NY (US)

( * ) Notice: Subject to any disclaimer, the term of this patent is extended or adjusted under 35 U.S.C. 154(b) by 0 days.

(21) Appl. No.: 17/588,944

(22) Filed: Jan. 31, 2022

(51) Int. Cl.
*A01H 5/08* (2018.01)
*A01H 6/00* (2018.01)

(52) U.S. Cl.
USPC ..... Plt./152
CPC ..... *A01H 6/00* (2018.05)

(58) Field of Classification Search
USPC ..... Plt./152, 216
CPC ..... A01H 5/0825
See application file for complete search history.

(56) References Cited

U.S. PATENT DOCUMENTS

| | | | |
|---|---|---|---|
| PP20,413 | P2 | 10/2009 | van Nijnatten |
| PP24,972 | P3 | 10/2014 | Mehlenbacher et al. |
| PP25,022 | P3 | 11/2014 | Mehlenbacher et al. |
| PP32,461 | P2 | 11/2020 | Molnar et al. |

OTHER PUBLICATIONS http://www.midwesthazelnuts.org/uploads/3/8/3/5/38359971/zs_nutty_ridge_llc_photon_and_nytka.pdf; Mar. 8, 2019; 15 pages.*

Henry et al., Planting Guide—American Hazelnut, Elsberry Plant Materials Center, Ellsbury MO, Dec. 2000.

Mc Cluskey et al., Yamhill Hazelnut, EM 8987-E, Oregon State Univ., Aug. 2009.

Rutter, P., Badgersett Research FArm—Plantings, Progects and Goals, NNGA Ann. Rep't, 1988, pp. 180-186.

Weschcke, C., Project Gutenberg; Growing Nuts in the North, Apr. 2006.

Coin, Glenn, "Will Mar. 2015 be one of the Coldest on Record" Syracuse Post—Standard, Mar. 23, 2015.

Zarnowski, J., Hazelnut Progress in New York, 2015.

Zarnowski, J., Z's Nutty Ridge Hazelnuts of Comercial Quality, Mar. 2019.

* cited by examiner

*Primary Examiner* — Kent L Bell

(74) *Attorney, Agent, or Firm* — Bernhard P. Molldrem, Jr.

(57) ABSTRACT

A new and interspecific hybrid *Corylus* named "Photon" characterized by cold hardiness, erect growth habit, the production of nuts with globular kernels that fall free of the husk at maturity and a high level of tolerance (quantitative resistance to eastern filbert blight caused by the fungus *Anisogramma anomala*).

5 Drawing Sheets

Latin nomenclature: *Corylus americana* X *Corylus avellana.*
Varietal denomination: Photon.
Inventors: Dawn Zarnowski, Jeffrey Zarnowski.

BACKGROUND OF THE INVENTION:

The present invention relates to a new and distinct cultivar of *Corylus* plant, botanically known as *Corylus americana* X *C. avellana* X *C.* unknown (a.k.a. *Corylus* hybr.) and the designation 'Photon' and hereinafter referred to by the name Photon. Originally designated F1R2-6 for Field #1, Row 2 in the $6^{th}$ position and then later designated P1 as one of the most promising trees to monitor.

The new *Corylus* cultivar resulted from corylan parents, one of which was an unnamed, unpatented *Corylus americana* hybrid plant which had been grown from an unnamed open-pollenated plant at Canton, Minn. 55922-9740, a USDA zone 4 location. The other parent was *Corylys avellana*. The resulting 'Photon' plant was an unnamed, unpatented planted in 2004 in Truxton, N.Y. (42° 40'N, 76° 1'W) on applicants' orchards.

We discovered 'Photon' as an outstanding cold hardy seedling out of over 3000 seedlings planted between 1995 and 2011 in The Orchard. 'Photon' flowered and produced normally after the very cold and record setting winters of 2013-2014 and 2014-2015 as recorded in nearby Syracuse N.Y.

'Photon' has been asexually reproduced via grafting and rooted suckers from 2015 through 2021. The unique features of this new *Corylus* plant are stable and are reproduced true-to-type in successive generations of asexual reproduction.

BRIEF SUMMARY OF THE INVENTION

The following traits have been observed and are determined to be the unique characteristics of 'Photon'. These characteristics in combination distinguish 'Photon' as a distinct cultivar:

Medium vigor and upright-spreading plant habit.

Yellowish-green to green color of developing and fully expanded leaves during the spring and into summer.

'Photon' exhibits exceptional cold hardiness amongst almost all seedlings from those parents. 'Photon' male and female flowers opened normally and the tree produced nuts normally in the record setting cold winters of 2014 and 2015. During the same period the majority of other hazelnut bushes in the field had make and/or female flowers. that did not open or set fruit due to cold injury in applicants' orchard (which is in USDA zones 5a/5b).

'Photon' is immediately distinguished from neighboring hazelnut bushes with prolific catkins in the spring. 'Photon' has an average of three catkins at most leaf buds and is a prolific pollen producer in most years.

'Photon' has showed no sign of diseased wood due to Eastern Filbert Blight (EFB), a disease caused by the fungus *Anisogramma anomala*. No fungicides to date are used to control EFB in The Orchard.

Based on field observations of 'Photon' in Truxton, N.Y., the nuts are ripe typically between the second week and fourth week in September. The period of ripening times can range from the last week in August to the first week in October. Husk length of 'Photon' is equal to nut length. Nuts are globular with round kernels that blanch fairly well that should be good for confection market and out of hand eating market. The kernel pellicle is free of any woodiness and appears nearly clear with a few light brown striations, prior to roasting, lending to the name 'Photon'.

Another unique trait of 'Photon' is that it is a shy bearer of suckers and only produces one sucker on average every other year in Truxton, N.Y. Coppicing failed to produce any suckers on the ortet in the season it was coppiced. 'Photon' may also be of substantial use as a cold-hardy, EFB-resistant non-suckering rootstock. Non-suckering trait is often associated with *Corylus colurna* commonly called Turkish tree hazel.

BRIEF DESCRIPTION OF DRAWINGS

The figures include color photographs that illustrate the overall appearance of the new cultivar, showing the colors as true as it is reasonably possible to obtain in colored reproductions of this type. Foliage colors in the photographs may differ slightly from the color values cited in the detailed botanical description which accurately describe the colors of this new *Corylus*.

DETAILED DESCRIPTION OF THE INVENTION

Figure 1:
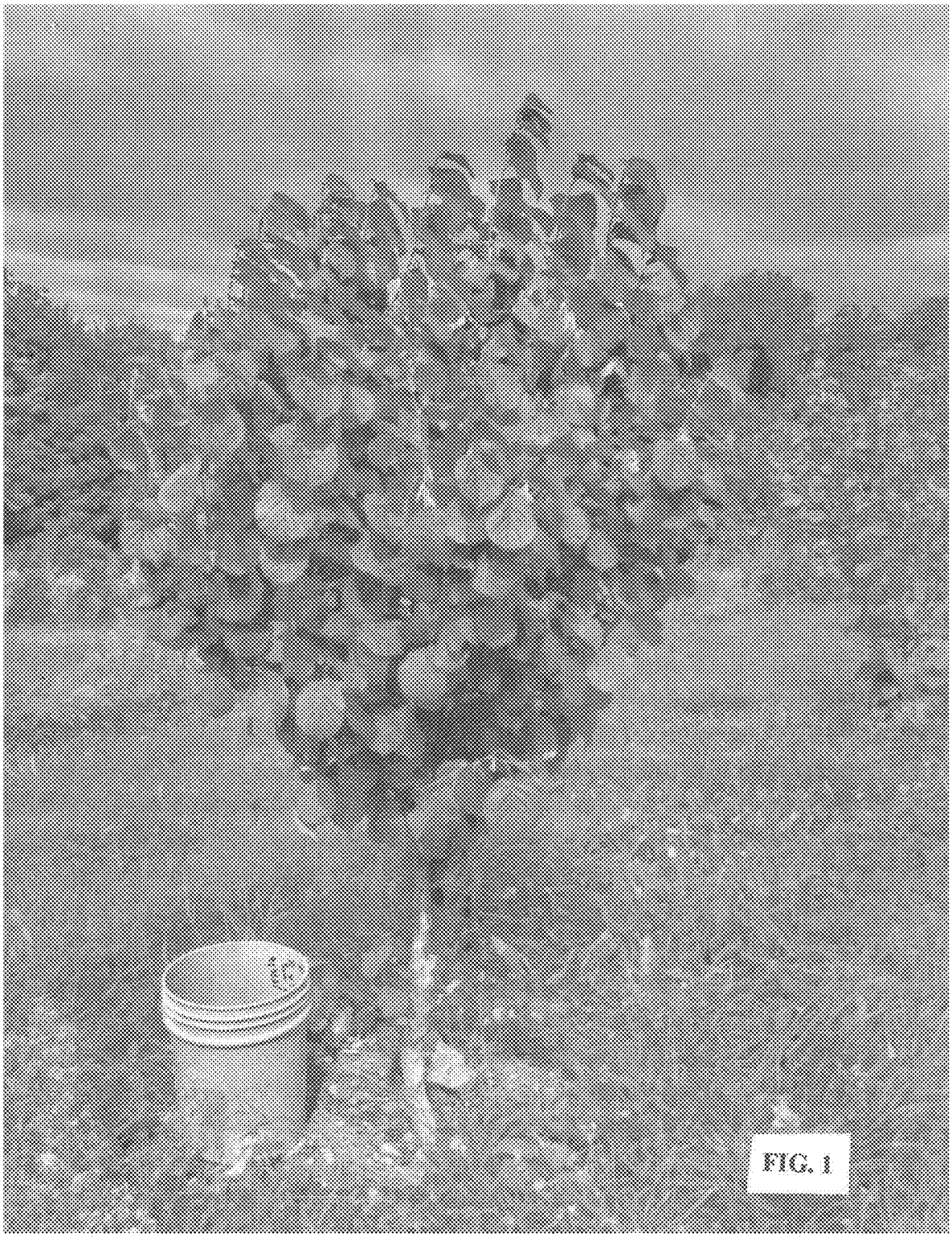
FIG. 1 is a color photograph of a tree of the new cultivar 'Photon' hazelnut in the six leaf.
Figure 2:
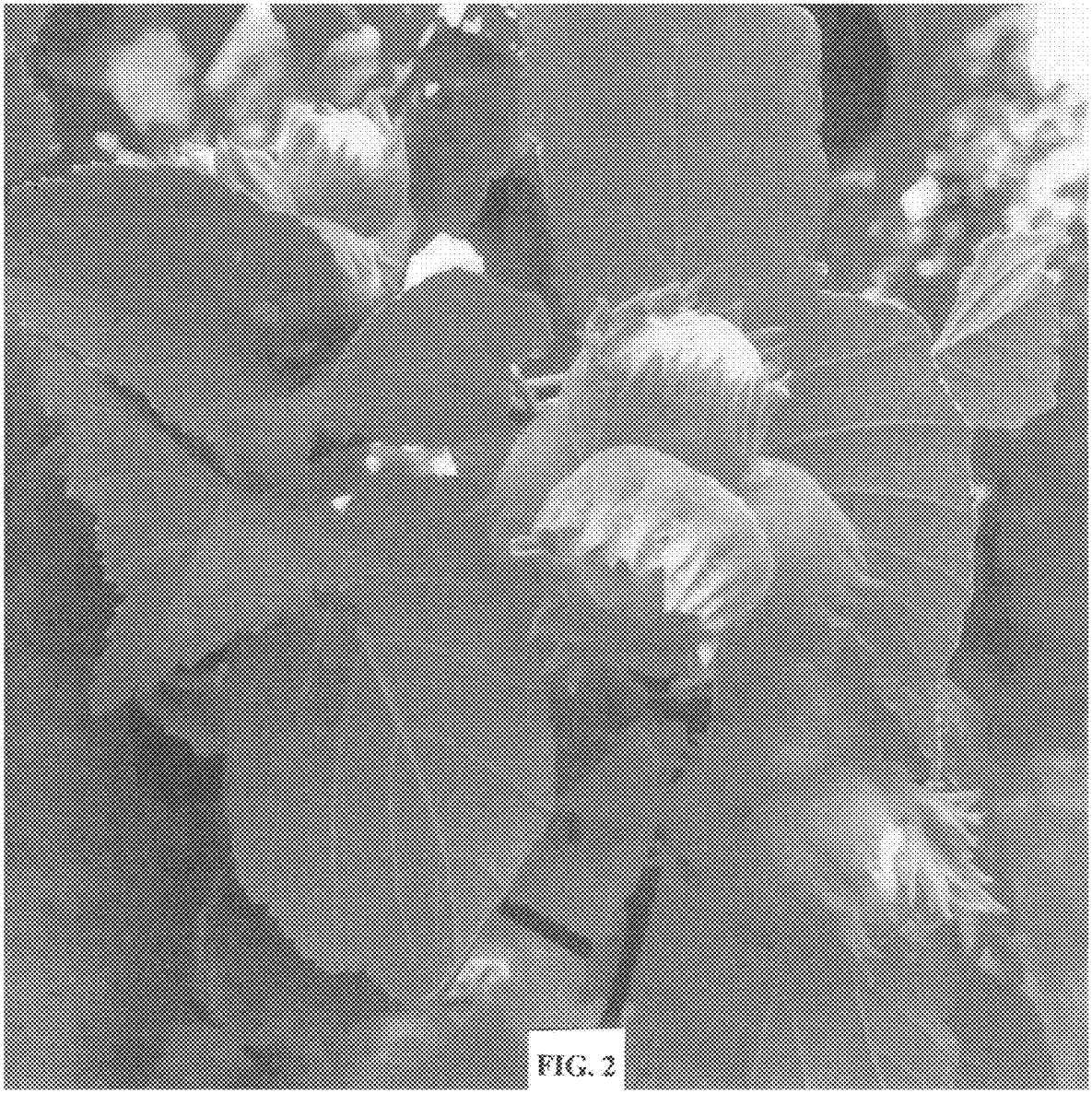
FIG. 2 is a color photograph of nuts, husks and leaves of the 'Photon' hazelnut cultivar.
Figure 3:
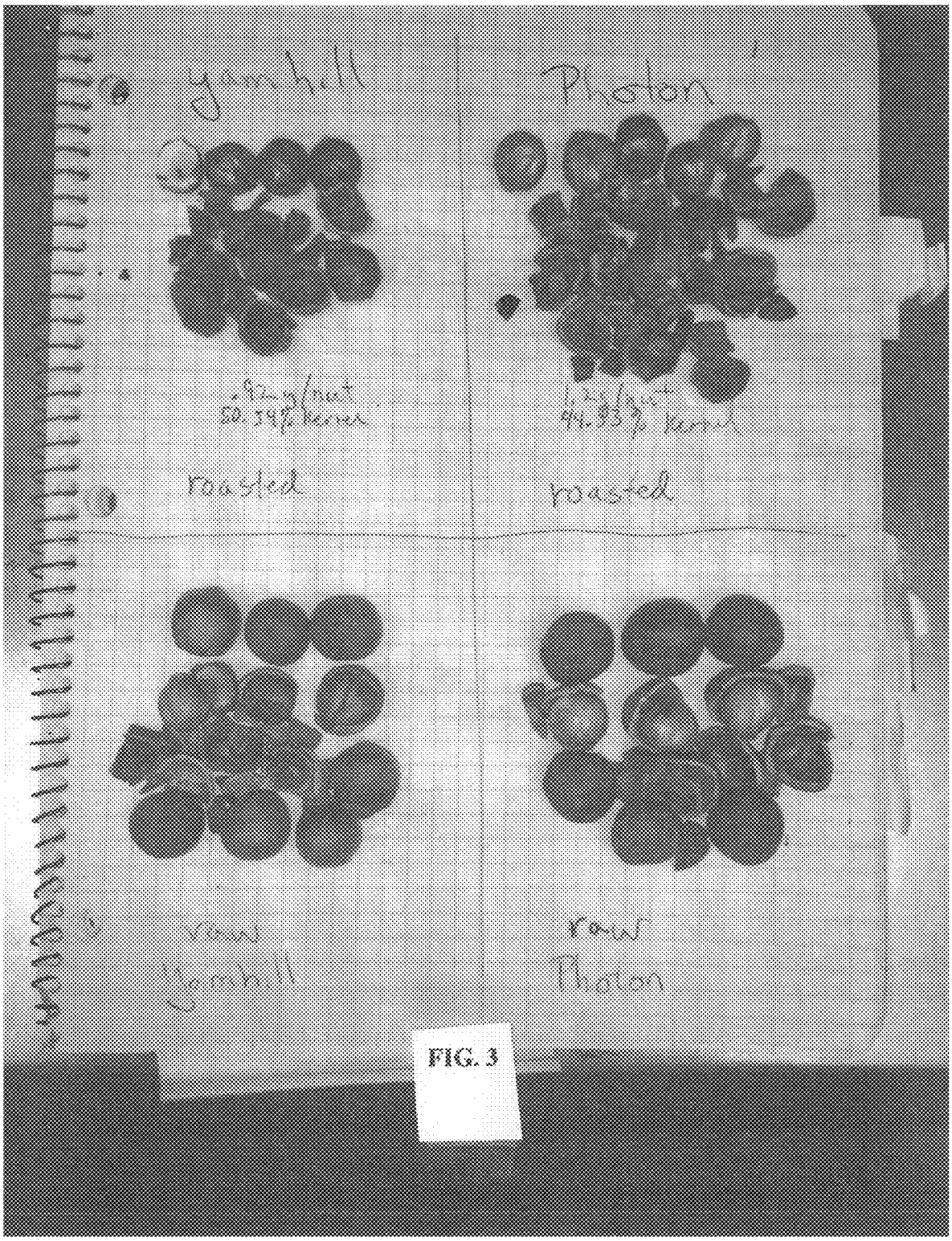
FIG. 3 is a color photograph of nuts, kernels and shells of the 'Photon' and 'Yamhill ' (unpatented) hazelnut cultivars.
Figure 4:
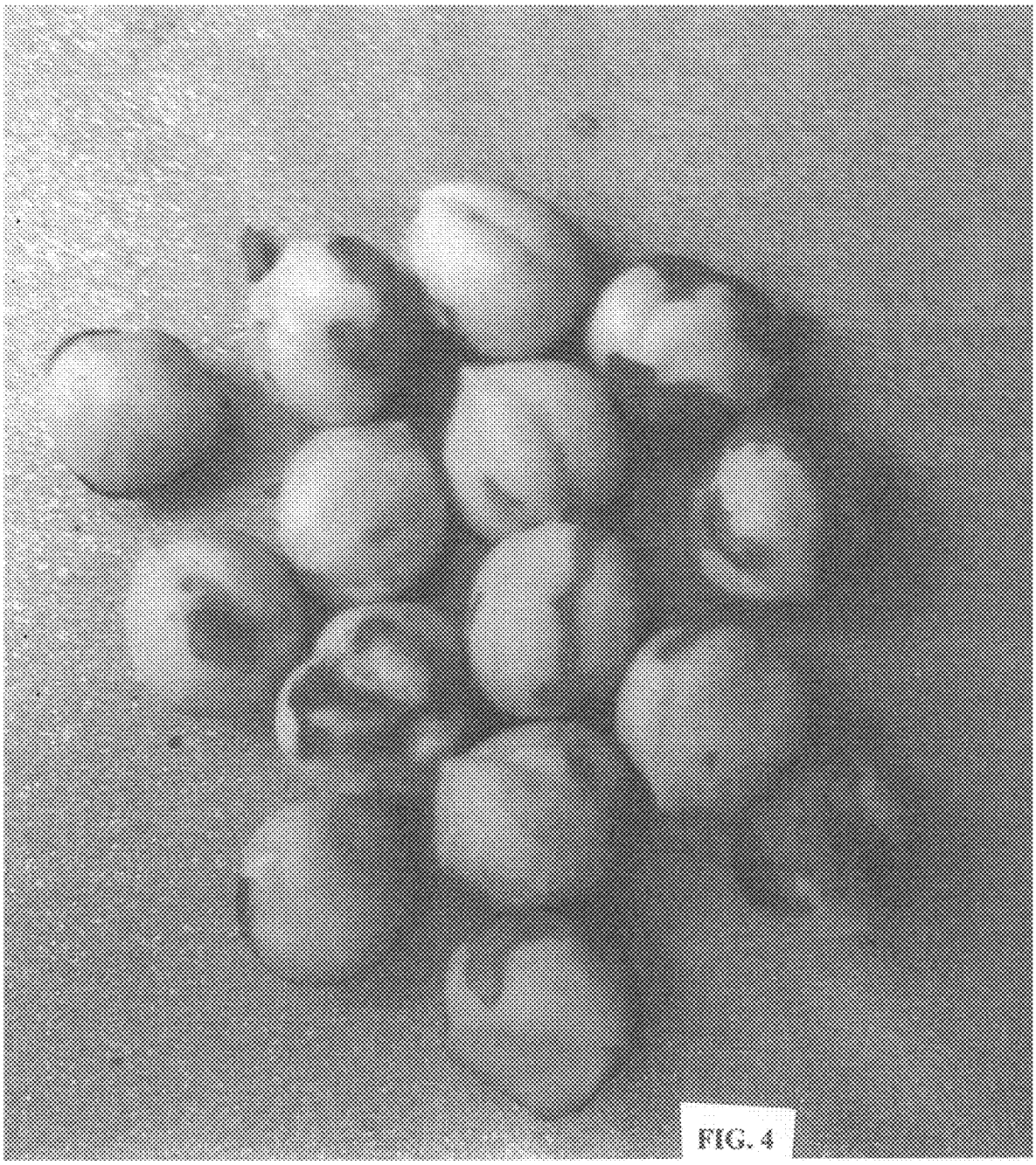
FIG. 4 is a color photograph of roasted nuts of the 'Photon' hazelnut cultivar.
Figure 5:
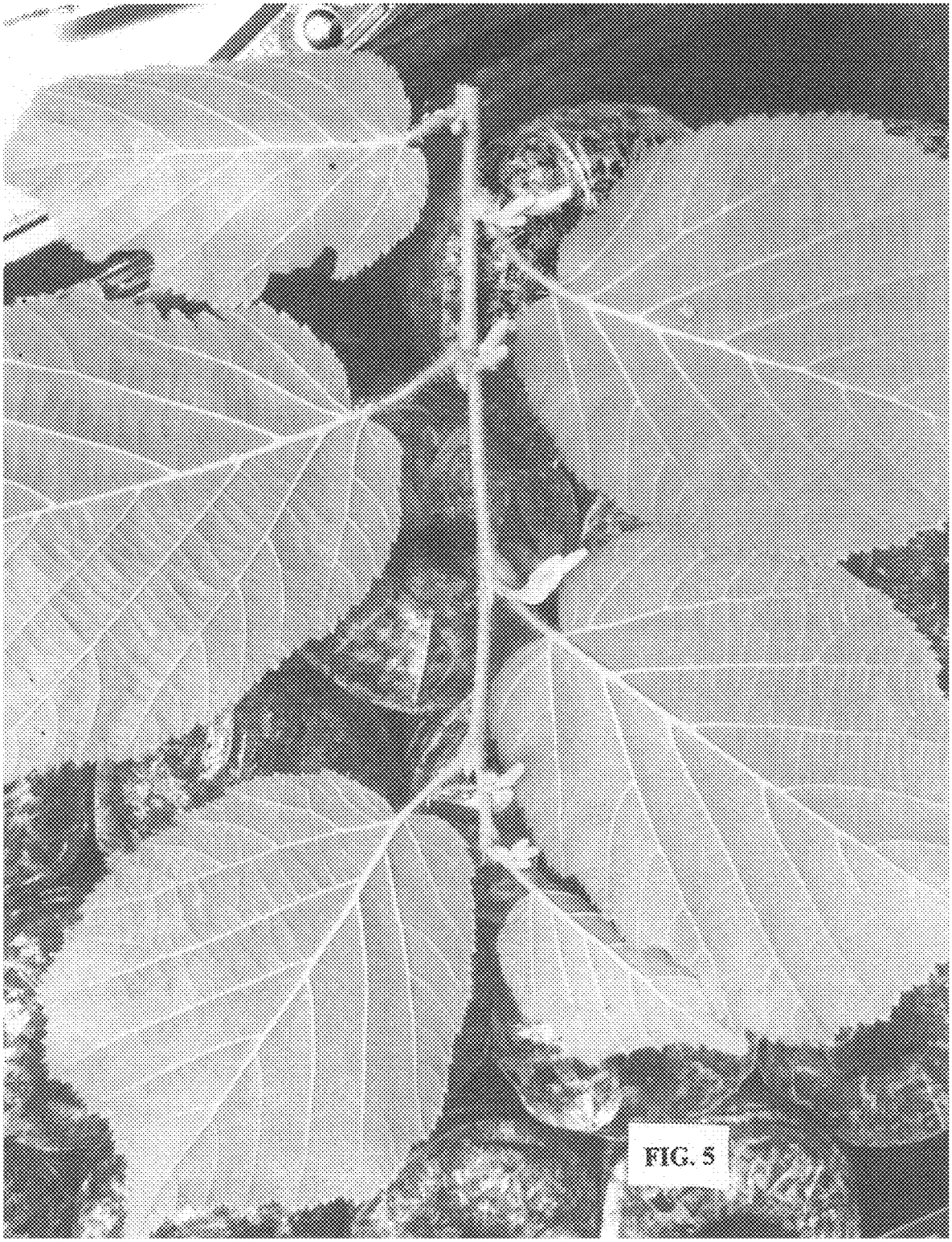
FIG. 5 is a color photograph of leaves and catkins of the 'Photon' hazelnut cultivar.

The cultivar 'Photon' has not been observed under all possible environmental conditions. The phenotype may vary somewhat with variations in environment such as temperature and light intensity, without, however, any variance in genotype.

The above-listed photographs together with the following observations and measurements show and describe plants grown in Truxton, N.Y., under commercial practice outdoors in the field during the spring and summer. Plants used for the photographs and description were from the original tree and from propagated trees, about six years old, from tie-off layerage and grown on their own roots.

In the following description, color references are made to *The Royal Horticultural Society Colour Chart,* 6th edition (2015), except where general terms of ordinary dictionary significance are used. *International Union for the Protection of New Varieties of Plants* ("UPOV") descriptors are described in the Mar. 28, 1979, UPOV Hazelnut guidelines.

Plant description:

- *General appearance*.—Natural habit is perennial shrub, but in commercial orchards, can be cultivated, using known plant husbandry, as a single trunk tree; rounded, erect plant habit.
- *Growth and branching habit*.—Freely branching; about 12 lateral branches develop per plant.
- *Vigor*.—Intermediate growth habit.
- *Branching density*.—Intermediate branching; about twelve lateral branches develop per plant.
- *Size*.—Plant height is about 3.3 meters at 18 years; plant diameter or spread is about 2.7 meters. Trunk at 30 cm above the soil line is 8.0 cm in 2021.
- *Trunk at* 30 *cm above the soil line*.—8.0 cm in 2021. Texture is mostly smooth, glabrous.
- *Trunk color*.—197D.
- *Suckering*.—Very weak.

Lateral branch description:

- *Length*.—About 18.5 cm; ranges from 12.0 cm to 24.0 cm.
- *Diameter*.—About 4.2 mm; ranges from 2.5 mm to 7.0 mm.
- *Internode length* (*at base*).—About 0.8 cm.
- *Internode length* (*at tip*).—About 4.0 cm; ranges from 2.0 cm to 6 cm.
- *Texture*.—Smooth, pubescent.
- *Strength*.—Strong.
- *Color, immature*.—146D.
- *Color, mature*.—147B.
- *Color of previous seasons branches*.—199B.

Foliage description:

- *Arrangement*.—Alternate, simple.
- *Length*.—About 8.9 cm; ranges from 7.8 cm to 10.2 cm.
- *Width*.—About 7.0 cm; ranges from 6.6 cm to 9.5 cm.
- *Shape*.—Ovate to round.
- *Apex*.—Obtuse to acute.
- *Base*.—Cordate.
- *Margin*.—Serrate.
- *Texture, upper and lower surfaces*.—Slightly pubescent.

*Venation pattern*.—Pinnate.

*Color, developing foliage*.—Upper surface 144B, lower surfaces, 144C.

*Color, fully expanded foliage, upper surface*.—Spring and summer, 137B; late summer and fall, 137B.

*Color, fully expanded foliage, lower surface*.—Spring and summer, 143B; late summer and fall, 143B.

*Color venation, upper surface*.—Spring and summer, 145B; late summer and fall, 145B.

*Color venation, lower surface*.—Spring and summer, 144B; late summer and fall, 144B.

Leaf bud description:

*Shape*.—Ovoid. Length; average 5.0 mm. Diameter: average 4.0 mm.

*Time of leaf budbreak*.—Medium to late, Descriptor-6; Photon budbreak is approximately one week after Yamhill.

*Color*.—145B.

Petiole description:

*Length*.—About 1.5 cm; ranges from 1.0 cm to 2.0 cm.

*Diameter*.—About 1.5 mm; ranges from 1.0 mm to 1.9 mm.

*Texture, upper and lower surfaces*.—Pubescent.

*Color*.—144B.

Flower description:

*Male inflorescences*.—Catkins.

*Color prior to elongation*.—176D.

*Catkin length prior to elongation*.—Average 28.0 mm.

*Catkin diameter*.—Average 4.5 mm.

*Male inflorescence length at full maturity*.—Average 5.7 cm.

*Catkin abundance*.—Dense, Descriptor-7.

*Female inflorescence style color*.—47B.

*Female inflorescence length at full maturity*.—Average 4.0 mm.

*Flowering precocity from sucker*.—1 year.

*Time of female flowering*.—Early to medium, Descriptor-4.

*Time of female flowering compared to male flowering*.—Same. Both male and female inflorescence may occur in late March in Truxton, N.Y.

*Time of male flowering*.—Early to medium, Descriptor-4.

*Involucre constriction*.—Present.

*Involucre length*.—Equal to length of nut, Descriptor-5.

*Size of indentation*.—Weak, Descriptor-3.

*Strength of serration of indentation*.—Weak, Descriptor-3.

*Thickness of callus at base*.—Medium, Descriptor-5

*Density of hairiness of involucre*.—Weak, Descriptor-3.

*Jointing of bracts*.—One on side.

Nut description:

*Length*.—Average 18.2 mm.

*Width*.—Average 18.5 mm.

*Thickness*.—Average 17.0 mm.

*Nut shape*.—Globular, Descriptor-2.

*Nut shape of cross section*.—Circular, Descriptor-2.

*Nut weight*.—Average 2.18 g.

*Kernel weight*.—Average 1.00 g.

*Kernel percentage* (*kernel weight/nut weight*).—Average 46.0%.

*Number of fruits per cluster*.—Two to three.

*Nutshell coloration*.—164A.

*Number of stripes on shell*.—Medium, Descriptor-5.

*Shape of fruit apex*.—Obtuse, Descriptor-2.

*Prominence of fruit apex*.—Slight to medium prominence, Descriptor-4.

*Size of fruit pistil scar on shell*.—Small, Descriptor-3.

*Hairiness of top of fruit*.—Medium, Descriptor-5.

*Curvature of nut basal scar*.—Flat, Descriptor-2.

*Double kernels*.—Absent, Descriptor-1.

*Kernel shape*.—Globular, Descriptor-2.

*Shape of kernel in cross-section*.—Globular, Descriptor-2.

*Lateral groove in kernel*.—Present.

*Corkiness of pellicle of kernel*.—Smooth, Descriptor-1.

*Color of fiber on the keel*.—166C.

*Color of pellicle under the fiber*.—Clear — 165C.

*Disease/pest resistance*.—These plants of 'Photon' exhibit a very high level of resistance to EFB. Plants have not been exposed to all possible strains of Anisogramma anomala present in North America. 'Photon' has not been thoroughly evaluated for tolerance of bud mites (*Phytoptus avellanae* Nal.); no bud mites were observed on the original tree or its propagules grown in Truxton, N.Y. Further, no bacterial blight caused by *Xanthomonas campestris* pv. *Corylina* was observed on the cultivar during the course of evaluations.

*Temperature tolerance*.—'Photon' was selected in Truxton, N.Y., and is targeted for production in USDA Plant Hardiness Zones 4 through 6. Plants of the new *Corylus avellana* have been observed to tolerate temperatures from −28 to 36° C. (−19° to 97° F.).

COMPARATIVE DATA

*Corylus americana* has a smaller growth habit compared *Corylus avellana* and natively grows as a bush with mature height typically from 1 meter to 3 meters. *Corylus americana* hasn't been used as a commercial crop due to much smaller nuts and thick shells compared to *Corylus avellana*. Breeding efforts with *Corylus americana* have only been in effect for a little over 100 years while *Corylus avellana* have been selected for thousands of years improving nut and growth characteristics. Common knowledge references and comparisons to how *Corylus avellana* grows in USDA zones 4 and 5 is limited due to the common lack of hardiness in combination with limited resistance if any to EFB. Hardiness and resistance to EFB makes *Corylus americana* genetically suitable for hybridization with other *Corylus* species to establish commercial orchards within its native North American range, instead of where EFB is absent and warmer climate suitable to *Corylus avellana*.

'Photon' is of average height for the *Corylus americana* hybrid in applicants' orchard. After 18 years it is 3.3 meters by 2.7 meters wide. It differs from the average *Corylus* hybrids with few suckers, prolific catkins most years, husk equals the length of the nut and globular shaped nuts with globular kernels. Nuts are also larger than average at Length of 18.2 mm, Width of 18.5 mm, and Thickness of 17 mm and very round. With 'Photon' parents being *Corylus avellana* that has a mature height of 4 to 6 meters and when hybridized to *Corylus americana* with mature heights of 1 to 3 meters, a mature height at 18 years of 3.5 meters for 'Photon' can be expected. *Corylus avellana* parent of 'Photon' typically have much larger nuts with thinner shells than the native *Corylus americana* nuts. *Corylus americana*

(parent of 'Photon') may have nuts that are typically 25 to 35% kernel as the nut is much smaller with thicker shells. Thus, nuts of 'Photon' carry the *Corylus avellana* nut traits while maintaining the blight resistance and cold hardiness of its *Corylus americana* parent. Production in years 2014 and 2015 when 'Photon' was 11 and 12 years old was 4.6 and 6.0 pounds of nuts respectively with rodent competition consuming a portion of the nuts prior to the nuts being ripe. Kernel to whole nut ratio of 'Photon' was 46% with kernels weighing 1.0 grams on average. Nuts drop free to the ground when ripe. Pellicle removal was 75 to 85%. Poorly filled nuts were 3.3% and blanks were 6.67%. Catkin length during pollen release is 2.5 to 3.5 inches long. Production in the year 2021 was 22 pounds of whole nuts.

In comparison, 'Yamhill' (not patented) is reported to have 1.1 grams of average kernel weight and 49% kernel by McCluskey, R. et. al. At applicants' orchard in 2021 the harvested 'Yamhill' kernel weight was 0.92 grams and 50.54 percent kernel percent to whole nut ratio and is comparable to what was reported by McCluskey, R. et.al. and 'Photon' averaged 1.2 grams kernel weight and 44.53 percent kernel to whole nut ratio. 'Photon' had a larger kernel but slightly lower kernel percent during 2014 than in 2021, with a kernel weight of 1.0 grams and kernel to whole ratio percentage of 46% and is typical for year-to-year differences depending on the growing degree days, precipitation nut set and care of the care of the applicants' orchard.

During the winter of 2015 the weather was 8 to 10 degrees (Fahrenheit) below average for the months of January through March and 12 to 16 degrees (F.) below normal for the month of February of 2015 for Cortland County, N.Y. During the spring of 2015 Photon catkins elongated, produced pollen with nut set occurring normally. All of the comparable releases planted in applicants' orchard including, 'Santiam' (np), 'Yamhill' (np), 'Lewis' (np), Dorris (U.S. Plant Pat. No. 25,022), 'Tonda Di Giffoni' (np), 'Sacajawea' (np) and York (U.S. Plant Pat. No. 24,942) failed to have catkins elongate due to winter desiccation in their third leaf (np).

'Photon' has showed no sign or 0.0% of diseased wood due to Eastern Filbert Blight (EFB) caused by the fungus *Anisogramma anomala* after 18 years, despite heavy EFB presence and death of hazel bushes from EFB in applicants' orchard. No fungicides to date are used to control EFB in applicants' orchard. In comparison, all clones planted in applicant's orchard have severe EFB lesions that include: two 'Jefferson', two York (U.S. Plant Pat. No. 24,972), one 'Sacajawea', two 'Dorris' (U.S. Plant Pat. No. 25,022), two 'Yamhill', two 'Santiam' and two 'Lewis'. The listed cultivars were planted in The Orchard in 2014. The comparable releases often fail to produce any nuts in USDA zones 5a and 5b in applicants' orchard. 'Jefferson' cultivars died within three years and 'Yamhill' can have lesions occupy 80% of the basal stem length leading to death of the stem. One 'Dorris', both 'York' and both 'Tonda Di Giffoni' have died due to a combination of EFB and lack of cold hardiness. Of the survivors 'Santiam' is the largest tree at 2.43 meters tall, with multiple stems that grow despite many EFB lesions being 61 cm. (24 inches) long and up to 101 cm. (40 inches) long. One 'Lewis' is only 1.22 meters (4 feet) tall and barely alive while the other 'Lewis' is 1.83 meters tall with up to 101 cm. long EFB lesions. The lone 'Dorris' tree is 2.13 meters tall with EFB lesions up to 122 cm. (48 inches) long.

REFERENCES

"Growing Nuts in the North," Carl Weschcke, https://www.gutenberg.org/files/18189/18189-h/18189-h.htm, WEBB PUBLISHING CO., ST. PAUL, MINN., U.S.A. Copyright 1954, pp. 25-38.

Rutter, P., "Badgersett Research Farm—Plantings, Projects, and Goals", NNGA 78 th Annual Report, 1987, pp. 180-186.

Will March 2015 be one of coldest on record in Central New York?—syracuse.com.

Zarnowski, J, "Hazelnut Progress in New York—Hardy nut trees are a must for a variable climate and sustainable agriculture that will replace annual grain crops.", New York Nut Growers Association, Summer, 2015

Zarnowski, J., "Z's Nutty Ridge azelnuts of Commercial Quality", Upper Midwest Hazelnut Development Initiative, March 2019, Eau Claire Wis. PowerPoint Presentation (midwesthazelnuts.org)

Henry, J and Kaiser, J. "Plantin Guide—American Hazelnut", USDA NRCS, Dec. 12, 2000, Microsoft Word—hazelguide.doc.(usda.gov)

McCluskey, R., Mehlenbacher, S. and Smith, D., "Yamhill Hazelnut", Oregon State University Extension Service, EM 8987-E, August 2009,

What is claimed is:

1. A new and distinct cultivar of *Corylus* plant, named 'Photon', as shown and described.

* * * * *